US00PP18168P2

(12) United States Plant Patent
Degenhardt

(10) Patent No.: US PP18,168 P2
(45) Date of Patent: Oct. 30, 2007

(54) *SEDUM* PLANT NAMED 'BON BON'

(50) Latin Name: *Sedum telephium*
Varietal Denomination: Bon Bon

(75) Inventor: Dick Degenhardt, Boskoop (NL)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 11/454,034

(22) Filed: Jun. 15, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Sedum* plant named 'Bon Bon', characterized by its upright and compact plant habit; freely basally branching habit; dense and bushy growth habit; brownish red-colored foliage; attractive red purple-colored flowers; and good garden performance.

1 Drawing Sheet

Botanical designation: *Sedum telephium.*
Cultivar denomination: 'Bon Bon'.

BACKGROUND OF THE INVENTION

The present invention relates to a new and distinct cultivar of *Sedum,* botanically known as *Sedum telephium* and hereinafter referred to by the name 'Bon Bon'.

The new *Sedum* originated from a cross-pollination made by the Inventor in 2002 in Boskoop, The Netherlands, of two unidentified selections of *Sedum telephium,* not patented. The new *Sedum* was discovered and selected by the Inventor as a single flowering plant within the progeny of the stated cross-pollination in a controlled environment in Boskoop, The Netherlands in 2002.

Asexual reproduction of the new *Sedum* by vegetative cuttings in a controlled environment in Boskoop, The Netherlands since 2002, has shown that the unique features of this new *Sedum* are stable and reproduced true to type in successive generations.

SUMMARY OF THE INVENTION

The cultivar Bon Bon has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Bon Bon'. These characteristics in combination distinguish 'Bon Bon' as a new and distinct cultivar of Sedum:

1. Upright and compact plant habit.
2. Freely basally branching habit; dense and bushy growth habit.
3. Brownish red-colored foliage
4. Attractive red purple-colored flowers.
5. Good garden performance.

Plants of the new *Sedum* differ from plants of the parent selections in the following characteristics:

1. Plants of the new *Sedum* are more compact than plants of the parent selections.
2. Plants of the new *Sedum* are more upright than plants of the parent selections.
3. Plants of the new *Sedum* and the parent selections differ in leaf and flower color as plants of the parent selections have green-colored foliage and pink-colored flowers.

Plants of the new *Sedum* can be compared to plants of the cultivar Garbro, disclosed in U.S. Plant Pat. No. 16,350. Plants of the new *Sedum* and the cultivar Garbro differ primarily in leaf and flower color as plants of the cultivar Garbro have olive green-colored leaves and lighter-colored flowers.

BRIEF DESCRIPTION OF THE PHOTOGRAPH

The accompanying colored photograph illustrates the overall appearance of the new *Sedum* showing the colors as true as it is reasonably possible to obtain in colored reproductions of this type. Colors in the photograph may differ slightly from the color values cited in the detailed botanical description which accurately describe the colors of the new *Sedum.* The photograph comprises a side perspective view of a typical flowering plant of 'Bon Bon' grown in an outdoor nursery.

DETAILED BOTANICAL DESCRIPTION

The aforementioned photograph and following observations, measurements and values describe plants grown in Boskoop, The Netherlands, under commercial practice during the summer in an outdoor nursery with day temperatures ranging from 14° C. to 32° C. and night temperatures ranging from 7° C. to 18° C. Plants were grown for about one year when the photograph and description were taken. In the following description, color references are made to The Royal Horticultural Society Colour Chart, 2001 Edition, except where general terms of ordinary dictionary significance are used.

Botanical classification: *Sedum telephium* cultivar Bon Bon.

Parentage:

*Female, or seed, parent.*—Unidentified selection of *Sedum telephium,* not patented.

*Male, or pollen, parent.*—Unidentified selection of *Sedum telephium,* not patented.

Propagation:

*Type.*—by vegetative cuttings.

*Time to initiate roots.*—About three weeks at 14° C.

*Root description.*—Thick, fleshy; yellowish grey in color.

*Rooting habit.*—Freely branching.

Plant description:

*Plant form/habit.*—Upright and compact plant habit; broad inverted triangle; moderately vigorous growth habit. Freely basally branching habit; dense and bushy growth habit.

*Plant height.*—About 36 cm.

*Plant width* (*spread*).—About 27.3 cm.

*Lateral branches.*—Length: About 17.6 cm. Diameter: About 2 mm. Internode length: About 5.4 cm. Strength: Moderately strong. Texture: Smooth, glabrous. Color: 187B.

Foliage description:

*Arrangement.*—Opposite, simple.

*Length.*—about 5.5 cm.

*Width.*—About 3.5 cm.

*Shape.*—Ovate.

*Apex.*—Rounded.

*Base.*—Cordate.

*Margin.*—Sparsely dentate.

*Texture, upper and lower surfaces.*—Smooth, glabrous; succulent.

*Venation pattern.*—Pinnate.

*Color.*—Developing leaves, upper surface: 187A. Developing leaves, lower surface: 146B; towards the margins, 183B. Fully expanded leaves, upper surface: N186C shaded with 146B; venation, 187C. Fully expanded leaves, lower surface: 148B; towards the margins, 187B; venation, 148B, towards the base, 187C.

Flower description:

*Flower type/habit.*—Small rotate flowers arranged in panicles; flowers face upright to slightly outward. Freely flowering habit with about 480 flower buds and flowers develop per plant.

*Fragrance.*—None detected.

*Natural flowering season.*—Continuously flowering from August though September in The Netherlands. Flowers persistent.

*Postproduction longevity.*—Flowers last about two weeks on the plant.

*Flower buds.*—Height: About 5 mm. Diameter: About 2.5 mm. Shape: Elliptic. Color: 185B; towards the base, N155C.

*Inflorescence height.*—About 2.6 cm.

*Inflorescence diameter.*—About 3.7 cm.

*Flower diameter.*—About 9 mm.

*Flower depth.*—About 5 mm.

*Petals.*—Quantity per flower: Typically five in a single whorl; petals fused at the base. Length: About 6 mm. Lobe width: About 2 mm. Shape: Narrowly ovate. Apex: Acute. Margin: Entire. Texture, upper and lower surfaces: Smooth, glabrous. Color: When opening, upper and lower surfaces: 59C. Fully opened, upper and lower surfaces: 59C; color becoming closer to 187B with development.

*Sepals.*—Quantity per flower: Typically five in a single whorl, fused at the base. Length: About 3 mm. Width: About 0.8 mm. Shape: Narrowly ovate. Apex: Acute. Margin: Entire. Texture, upper and lower surfaces: Smooth, glabrous. Color: When opening, upper and lower surfaces: 180A to 180B. Fully opened, upper and lower surfaces: 148A, speckled with 58A.

*Peduncles.*—Length: About 1.2 cm. Diameter: About 1 mm. Angle: About 30° from vertical. Strength: Moderately strong. Texture: Smooth, glabrous. Color: 187B.

*Pedicels.*—Length: About 4 mm. Diameter: About 0.8 mm. Angle: Erect to about 45° from vertical. Strength: Moderately strong. Texture: Smooth, glabrous. Color: 148A, speckled with 58A to 184A.

*Reproductive organs.*—Stamens: Quantity per flower: Typical ten. Filament length: About 3 mm. Filament color: N155C to 186D. Anther shape: Oblong, flattened. Anther length: About 0.5 mm. Anther color: 200A to N200A. Pollen amount: Scarce. Pollen color: Close to 14A. Pistils: Quantity per flower: Five. Pistil length: About 4.5 mm. Stigma shape: Pointed. Stigma color: 184B to 184C. Style length: About 4 mm. Style color: 154D. Ovary color: 154D.

*Seed/fruit.*—Seed and fruit development have not been observed.

Disease/pest resistance: Plants of the new *Sedum* have not been noted to be resistant to pathogens and pests common to *Sedum.*

Garden performance: Plants of the new *Sedum* have been observed to have good garden performance and tolerance rain, wind and are winter hardy in The Netherlands.

It is claimed:

1. A new and distinct *Sedum* plant named 'Bon Bon' as illustrated and described.

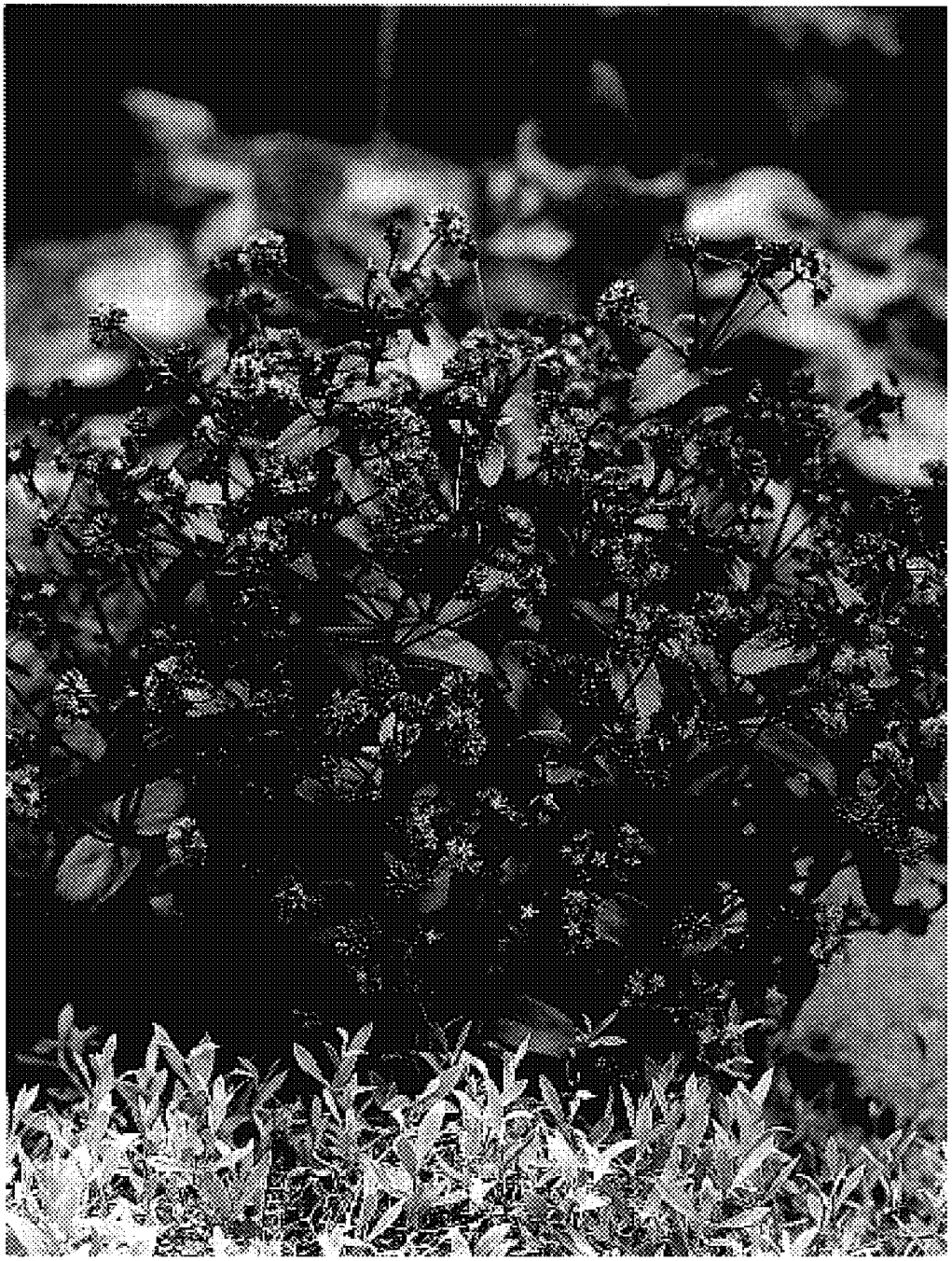

* * * * *